United States Patent [19]

Lin et al.

[11] Patent Number: 4,628,018
[45] Date of Patent: Dec. 9, 1986

[54] SILYLATED COMPOSITIONS, AND DEUTERATED HYDROXYL SQUARAINE COMPOSITIONS AND PROCESSES

[75] Inventors: John W. Lin; Lesley P. Dudek, both of Webster, N.Y.

[73] Assignee: Xerox Corporation, Stamford, Conn.

[21] Appl. No.: 766,326

[22] Filed: Aug. 16, 1985

Related U.S. Application Data

[62] Division of Ser. No. 613,137, May 23, 1984, Pat. No. 4,585,884.

[51] Int. Cl.⁴ .......................... G03G 5/06; G03G 5/14
[52] U.S. Cl. ......................................... 430/59; 430/58
[58] Field of Search ................... 430/58, 59

[56] References Cited

U.S. PATENT DOCUMENTS

4,415,639  11/1983  Horgan ..................... 430/59 X

Primary Examiner—Roland E. Martin
Attorney, Agent, or Firm—E. O. Palazzo

[57] ABSTRACT

Disclosed are novel silylated hydroxyl squaraine compositions, novel deuterated hydroxyl squaraine derivatives, and processes for the preparation thereof. More specifically, there is disclosed a process for the preparation of photoconductive hydroxyl squaraine pigment compositions useful as visible and near infrared photoconductor materials comprising (1) effecting functionalization of the hydroxyl squaraine in an organic solvent system wherein the hydroxyl group therein are silylated, and (2) subjecting the resulting silylated products to hydrolysis enabling conversion to purified squaraine compositions, or conversion to deuterated hydroxyl squaraine derivatives. The hydroxyl squaraine compositions obtained are useful, for example, as photogenerating pigments in layered imaging members.

23 Claims, 4 Drawing Figures

FIG. 1
(CONFIGURATION 1)

FIG. 2
(CONFIGURATION 2)

FIG. 3
(CONFIGURATION 3)

FIG. 4
(CONFIGURATION 4)

SILYLATED COMPOSITIONS, AND DEUTERATED HYDROXYL SQUARAINE COMPOSITIONS AND PROCESSES

This is a division of application Ser. No. 613,137, filed May 23, 1984, now U.S. Pat. No. 4,585,884.

BACKGROUND OF THE INVENTION

This invention relates generally to new compositions of matter and improved processes for the preparation thereof. More specifically, the present invention is directed to novel silylated hydroxyl squaraine compositions, novel deuterated hydroxyl squaraine derivatives, and to processes for preparing these compositions. The silylated products are primarily useful as colorants, and as intermediates for the preparation of hydroxyl squaraine derivatives, while the deuterated hydroxyl squaraine derivatives are useful as photoconductive compositions. Thus, for example the hydroxyl squaraines obtained from the silylated products of the present invention can be incorporated into layered photoresponsive imaging members, or devices, which members are responsive to visible light, and infrared illumination orginating in laser printing systems. The photoresponsive members envisioned can, for example, contain situated between a bottom photogenerating layer and a top hole transport layer, or situated between a top photogenerating layer and a bottom hole transporting layer and a supporting conductive substrate, a photoconductive composition, comprised of the squaraine compositions, especially the deuterated and nondeuterated hydroxyl squaraine derivatives prepared from the silylated products illustrated herein. Examples of other photoresponsive devices include those comprised of a conductive substrate, a hole transport layer, and as a top layer photoconductive hydroxyl squaraine derivatives; or wherein the photoconductive squaraine layer is situated between a conductive substrate and a hole transport layer. The photoconductive squaraine compositions are partially or totally responsible for enhancing the intrinsic properties of the photogenerating layer in the infrared and visible regions of the spectrum, thereby allowing the resulting imaging members to be sensitive to infrared and/or visible light.

Additional photoresponsive devices include those containing the photoconductive squaraine compositions in contact with a hole transport layer deposited on a supporting substrate with optional blocking and adhesive layers, and a protective top layer; or a similar device wherein the photoconductive layer is situated between the hole transport layer, and a supporting substrate. Other specific photoconductive devices included within the scope of the present invention are those comprised of a supporting substrate, an optional blocking layer, a photogenerating layer containing inorganic photoconductive materials, such as trigonal selenium, or organic photoconductive materials including phthalocyanines, a photoconductive layer comprised of the hydroxyl squaraine compositions, and a top hole transport layer. In a variation of the latter device, the hydroxyl squaraine photoconductive material can be located on the supporting substrate, or between the hole transport layer and the photogenerating layer. Several of these devices are illustrated in U.S. Pat. No. 4,415,639 entitled Layered Photoresponsive Devices, the disclosure of which is totally incorporated herein by reference.

Photoconductive imaging members containing certain squaraine compositions, particularly hydroxyl squaraines, are known, as described for example in U.S. Pat. Nos. 3,617,270 and 3,824,099. Further, there is described in a review article by Arthur H. Schmidt, SYNTHESIS, pages. 961-994, 1980 and the references therein, several methods for preparing squaric acid and squaraine derivatives including hydroxyl squaraines. Also known are layered photoresponsive devices with photogenerating layers and transport layers, reference U.S. Pat. No. 4,265,990. Examples of photogenerating layers disclosed in this patent include trigonal selenium, and phthalocyanine derivatives, while examples of transport layers that may be selected include certain aromatic amines and aromatic diamines dispersed in a resinous binder composition. Moreover, the use of specific squaraine pigments in photoresponsive imaging devices was disclosed in U.S. Pat. No. 4,415,639 entitled Layered Photoresponsive Devices wherein there is described an improved photoresponsive device containing a substrate, a hole blocking layer, an optional adhesive interface layer, an inorganic photogenerating layer, a photoconductive composition capable of enhancing the intrinsic properties of the photogenerating layer, and a hole transport layer. As photoconductive compositions for these devices, there can be selected various hydroxyl squaraine pigments. Additionally, there was disclosed in U.S. Pat. No. 3,824,099 certain photosensitive hydroxyl squaraine compositions. According to the disclosure of this patent, the squaraine compositions are photosensitive in normal electrophotographic imaging systems.

In a copending application, there are described novel squaraine compositions of matter, including bis-9-(8-hydroxyjulolidinyl)squaraine, and the use of these compositions in imaging members. One of the imaging members illustrated contains a supporting substrate, a hole blocking layer, an optional adhesive interface layer, an inorganic photogenerating layer, a julolidinyl photoconducting composition layer capable of enhancing the intrinsic properties of the photogenerating layer and a hole transport layer.

Processes for preparing squaraine compositions generally involve the reaction of squaric acid with an aromatic amine. Thus, for example, the julolidinyl squaraine compositions can be prepared by the reaction of an aromatic amine and squaric acid, in a molar ratio of from about 1.5:1 to 3:1 in the presence of a mixture of an aliphatic alcohol, and an optional azeotropic cosolvent. About 200 milliliters of alcohol to 0.1 mole of squaric acid are used, while from about 40 milliliters to about 4,000 millilters of an azeotropic material, such as benzene, toluene, or the like are selected. The squaric acid coupling reaction is generally accomplished at a temperature of from about 50 degrees Centigrade to about 130 degress Centigrade. Illustrative examples of aromatic amine reactants include 8-hydroxyjulolidine, 3-dimethylaminophenol 3-diethylaminophenol and the like while examples of aliphatic alcohols include 1-butanol, 1-pentanol and 1-octanol.

Additionally, there is described in another copending application the preparation of novel squaraine compositions, including for example, bis(4-N,N-dimethylamino-2-hydroxy-6-methylphenyl)squaraine by the reaction of squaric acid and 3-hydroxy-5-methyl-N,N-dimethylaniline(3-N,N-dimethylamino-5-methyl-phenol). More specifically, as disclosed in this copending application the squaraine compositions involved are prepared by suspending squaric acid in an alcohol, followed by heating. Subsequently, there is then added to the resulting mixture an aromatic amine, such as 3-dialkylaminomethylphenol. This reaction is generally accomplished at a temperature of from about 50° C. to about 130° C. with stirring, wherein the desired product is isolated from the reaction mixture by known techniques and identified by analytical tools including NMR, mass spectroscopy and elemental analysis for carbon, hydrogen, oxygen and nitrogen.

While the above processes for preparing squaraine compositions may be suitable for their intended purposes, there continues to be a need for other processes wherein squaraine compositions, useful as photoconductive materials, can be prepared. Additionally, there remains a need for simple, economical processes for preparing squaraine compositions, wherein the squaraine products obtained are of higher purity, and smaller particle size than those obtained with many of the prior art processes. It is believed that the presence of impurities in the squaraine compositions causes the photosensitivity of these compositions to vary significantly, and in many instances, to be lower than the squaraine compositions prepared in accordance with the process of the present invention. Further, there continues to be a need for processes for the preparation of squaraine compositions, especially hydroxyl squaraines, of high purity, small pigment particle size, and improved morphological properties which, when selected for layered photoresponsive imaging devices, allow the generation of acceptable images, and wherein such devices can be repeatedly used in a large number of imaging cycles without deterioration thereof from the machine environment or surrounding conditions. Moreover, there remains a need for certain squaraine compositions, wherein the resulting products when incorporated into imaging members exhibit excellent pigment dispersion with uniform surface coverage, and superior sensitivity. Additionally, there is a need for processes for the preparation of photosensitive pigments containing novel deuterated hydroxyl squaraines. There also continues to be a need for processes of preparing hydroxyl squaraines, and novel deuterated hydroxyl squaraines, which possess high photosensitivity characteristics and desirable small particle sizes, enabling their use as photosensitive pigments with increased and consistent photosensitivity. Moreover, there remains a need for novel silylated products, which subsequent to hydrolysis are converted into deuterated and nondeuterated hydroxyl squaraine derivatives as indicated herein.

SUMMARY OF THE INVENTION

It is therefore an object of the present invention to provide improved processes for preparing squaraine compositions.

In another object of the present invention there are provided methods for the functionalization of photoconductive squaraine compositions containing hydroxyl groups, enabling silylated products with enhanced solubility in organic solvents.

In yet another object of the present invention, there are provided simple, economical processes for preparing certain squaraine compositions with high purity levels, and less occluded impurities than similar hydroxyl squaraine derivatives prepared by several known methods.

In still a further object of the present invention, there are provided improved processes for obtaining squaraine compositions of matter, which contain particles of substantially smaller particle sizes than similar hydroxyl squaraines prepared by many known processes.

In another object of the present invention, there are provided improved processes for preparing certain squaraine compositions with enhanced photosensitivity, good dark decay properties and acceptable charge acceptance.

In another object of the present invention there are provided improved processes for preparing squaraine compositions, with enhanced photosensitivity in the visible and near infrared regions of the spectrum.

In yet another object of the present invention there are provided improved processes for preparing photosensitive pigments with desired particle sizes, and improved morphological characteristics, by the controlled hydrolysis of silylated hydroxyl squaraine derivative products.

In yet another object of the present invention there are provided improved methods for preparing novel deuterated photoconductive hydroxyl squaraine derivatives, which are photosensitive in the visible and near infrared regions of the spectrum.

In still another object of the present invention there are provided processes for the preparation of hydroxyl squaraine derivatives of high purity and effective small particle sizes, enabling their presence in high density in a photoconductive layer, thereby enhancing image resolution and photosensitivity of the photoreceptor involved.

In a further object of the present invention there are provided novel silylated compositions of matter which are useful as colorants and which can function as intermediates in that subsequent to hydrolysis, the silylated products are converted to useful hydroxyl squaraine derivatives.

These and other objects of the present invention are generally accomplished by the provision of novel silylated hydroxyl squaraine derivative compositions, improved hydroxyl squaraine derivatives, novel deuterated hydroxyl squaraine derivatives, processes for preparing these compositions, and photoconductive imaging members containing hydroxyl squaraine derivatives and deuterated hydroxyl squaraine derivatives. More specifically, there is provided in accordance with the present invention novel silylated compositions, and deuterated hydroxyl squaraine derivatives of the following formulas:

I. Silylated Products

SYMMETRICAL

UNSYMMETRICAL

II. Deuterated Hydroxyl Squaraine Derivatives

SYMMETRICAL

UNSYMMETRICAL wherein $R_1$ and $R_2$ are independently selected from alkyl groups, aromatic groups, cyclic groups, including julolidinyl substituents, and non-cyclic groups, including substituted alkyl groups, X is selected from the group consisting of oxygen, sulfur, and selenium, $R_3$, $R_4$ and $R_5$ are independently selected from hydrogen, alkyl groups, halides, alkoxy, alkyl carboxy, and the like; and $R_6$, $R_7$ and $R_8$ represent appropriate groups attached to siloxyl groups, including alkyl substituents, halogenated substituents, oxygenated substituents, and the like, D is a deuterium atom, $R'_1$, $R'_2$, $R'_3$ and $R'_4$ are independently selected from alkyl groups, aromatic groups, cyclic groups, and non-cyclic groups, providing that at least one of these groups is dissimilar, $R'_5$, $R'_6$, $R'_7$, $R'_8$, $R'_9$, $R'_{10}$ and $R'_{11}$ are independently selected from hydrogen, alkyl groups, halides, alkoxy and alkyl carboxy groups, and $R'_{12}$, $R'_{13}$ and $R'_{14}$ are selected from alkyl substituents, halogenated substituents, oxygenated substituents and the like.

The silylated products as indicated herein are useful for example as colorants in that in solution they absorb light of a wavelength ranging near 649 nanometers and further these novel compositions can be used as intermediates for the formation of hydroxyl squaraine derivatives by a hydrolysis reaction as illustrated hereinafter. The resulting hydroxyl squaraine derivatives can then be selected as a photoconductive pigment for incorporation into a layered photoresponsive device sensitive to visible light, and/or infrared illumination. Similarly, the novel deuterated hydroxyl squaraine derivatives obtained by the hydrolysis of the silylated compositions, in a deuterated protonic solvent system, are useful as photoconductive pigments for incorporation into layered photoresponsive devices which are sensitive to visible light, and/or infrared illumination.

Also in accordance with the present invention there is provided a silylation process for the purification of squaraine compositions containing hydroxyl functional groups therein. The intermediate products are of enhanced solubility in various organic solvents, enabling undesirable impurities to be removed therefrom. Subsequent to hydrolysis of the resulting functionalized product in deuterated, or non-deuterated solvents, including alcohols, water, and mixtures thereof, there results for example compositions containing less impuriries therein than the initial squaraine reactant. When deuterated solvents are selected, there is obtained in accordance with the process of the present invention novel deuterated hydroxyl squaraine compositions. More specifically in one embodiment, the process of the present invention comprises silylating certain hydroxyl squaraine compositions with known silylation reagents, at a temperature of from about zero degrees Centigrade to about 155 degrees Centigrade, resulting in products containing silyl ether groups thereon including trialkylsiloxyl groups, which compositions have improved solubility in organic solvents enabling the preparation of hydroxyl squaraines or deuterated hydroxyl squaraines, of improved purity, and thus improved sensitivity, subsequent to hydrolysis. During this process the undesirable occluded impurities present in the hydroxyl squaraine pigments are released therefrom. Removal of the undesirable soluble impurities can, for example, be achieved by separating the precipitated product from the reaction mixture by known methods. Further, insoluble impurities which may be present in the hydroxyl squaraine composition reactant can be separated therefrom by dissolving the formed silylated product in halogenated solvents, like methylene chloride, chloroform and trichloroethane, followed by filtration and evaporation of the solvent selected. Also the solution containing the soluble silylated hydroxyl squaraine can be purified by known chromatographic techniques, and thereafter the purified silylated derivatives can be isolated therefrom, by evaporation.

Subsequently, the silylated product is hydrolyzed in a suitable solvent system at an effective temperature so as to result in a hydroxyl squaraine of higher purity than the initial hydroxyl squaraine, and wherein the resulting hydroxyl squaraine composition is of a smaller average particle/crystallite size than the initial hydroxyl squaraine reactant. Moreover, novel hydroxyl squaraine compositions can be prepared by effecting the hydrolysis in the presence of a deuterated composition enabling the preparation of deuterated hydroxyl squaraines of high purity and small average particle/crystallite sizes.

There is illustrated in the following equations specific examples for preparing symmetrical silylated products (reactions I and II), hydroxyl squaraine derivatives (reaction III) and deuterated hydroxyl squaraine derivatives (reaction IV). This reaction scheme can also be selected for the preparation of related unsymmetrical compositions.

wherein the substituents are as defined herein.

The hydroxyl squaraine derivatives selected for silylation are generally derived from the condensation products of hydroxyl aromatic amines, and squaric acid. More specifically, these hydroxyl squaraine derivatives can be in various isomeric forms, including cis and trans isomers and may have symmetrical or unsymmetrical groups (mixed squaraines) thereon and attached to the central squaric acid moiety. Moreover, it is important to note that the silylation reaction illustrated, and the subsequent hydrolysis process are applicable to virtually any hydroxyl squaraine derivatives providing they contain therein a functionalizable hydroxyl (—OH) or thio (—SH) group. Thereafter as illustrated the resulting silylated product can be hydrolyzed. Alternatively the silylated product can be dissolved in a suitable organic solvent wherein the insoluble impurities are removed, followed by hydrolysis of the soluble product.

Alkyl substituents include those containing from about 1 carbon atom to about 10 carbon atoms, and preferably from 1 carbon atom to about 4 carbon atoms like methyl, ethyl, propyl, butyl, pentyl, hexyl, heptyl, octyl, nonyl and decyl. Preferred alkyl groups are methyl, ethyl, propyl and butyl. Examples of alkylcarboxy substituents include methylcarboxy, ethylcarboxy, propylcarboxy, butylcarboxy, and the like. Examples of aromatic groups include those containing from about 6 to about 24 carbon atoms, such as phenyl, and naphthyl, while alkoxy groups include those containing from about 1 to about 6 carbon atoms, such as methoxy, ethoxy, propoxy, and the like. Illustrative examples of cyclic groups are julolidinyl substituents, while carboxy groups envisioned include alkylcarboxy, such as methylcarboxy.

Illustrative examples of squaraine compositions with improved purity and other desirable characteristics, including small particle sizes, deuterated squaraine compositions, and novel silylated materials prepared in accordance with the process of the present invention include known hydroxyl squaraine derivatives such as bis(2-hydroxy-4-N,N-dimethylaminophenyl)squaraine, bis(2-hydroxy-4-N,N-diethylaminophenyl)squaraine, bis(2-hydroxy-6-methyl-4-N,N-dimethylaminophenyl)squaraine, bis-9-(8-hydroxyjulolidinyl)squaraine; hydroxyl deuterated squaraine derivatives including bis(2-deuterated hydroxy-4-N,N-dimethylaminophenyl)squaraine, bis(2-deuterated hydroxy-4-N,N-diethylaminophenyl)squaraine, bis(2-deuterated hydroxy-6-methyl-4-N,N-dimethylaminophenyl)squaraine, bis-9-(8 deuterated hydroxy julolidinyl)squaraine; unsymmetrical squaraines, such as 2-hydroxy-4-N,N-dimethylaminophenyl-4'-N',N'-dimethylaminophenyl squaraine, 2-hydroxy-4-N,N-dimethylaminophenyl-2'-methyl-4'-N',N',-dimethylaminophenyl squaraine, 2-hydroxy-4-N,N-dimethylaminophenyl-2'-fluoro-4'-N',N',-dimethylaminophenyl squaraine, 2-hydroxy-4-N,N-dimethylaminophenyl-2'-chloro-4'-N',N',-dimethylaminophenyl squaraine; bis(2-trimethylsiloxy-4-N,N-dimethylaminophenyl)squaraine, bis(2-trimethylsiloxy-4-N,N-diethylaminophenyl)squaraine, bis(2-trimethylsiloxy-6-methyl-4-N,N-dimethylaminophenyl)squaraine, bis-9-(8-trimethylsiloxyjulolidinyl)-squaraine; and the like.

It is appreciated that the process of the present invention can be selected for the preparation of other squaraine compositions including symmetrical and unsymmetrical squaraine derivatives containing for example, hydroxyl, and/or thiol groups therein. Accordingly, the process of the present invention is not limited to the specific illustrative reactions, or reaction parameters provided.

There can be selected for the silylation reaction known reagents as described in the literature, and the textbook Silylation of Organic Compounds, by Alan E. Pierce, of Pierce Chemical Company, Rockford, Ill., 1979, the appropriate disclosure of which is totally incorporated herein by reference. Specific examples of useful silylation reagents include N,O-bis-(trimethylsilyl)-acetamide (BSA), N,O-bis-(trimethylsilyl)trifluoroacetamide (BSTFA), N-methyl-N-trimethylsilyltrifluoroacetamide (MSTFA), N-trimethylsilyl diethylamine (TMSDEA), hexamethyldisilazane (HMDS), trimethylchlorosilane (TMCS), N-trimethylsilylimidazole (TMSI), and the like.

Known dried organic solvents selected for the silylation reaction include dimethylformamide, pyridine, tetrahydrofuran, chloroform, toluene, ethers, dimethylsulfoxide, ethylacetate, and the like. Other solvents can be selected providing the objectives of the present invention are achieved, that is those solvents that will allow the silylation of the hydroxyl groups to be accomplished without resulting in undesirable side reactions which may permanently degrade or adversely affect the physical properties of the reactants and the resulting products.

The silylation reaction can be monitored, for example, by infrared spectroscopy using Nujol Mull (mineral oil) as a dispersing medium. Certain IR absorption bands associated with the hydroxyl groups of the squaraine compositions selected will diminish upon silylation accompanied by an increase in the intensity of new peaks attributed to the presence of trimethylsiloxy groups.

Hydrolysis is effected by adding to the separated silylated product an effective amount of a solvent system comprised of for example water and/or alcohols, and maintaining the resulting mixture at an appropriate temperature. Additionally, the hydrolysis reaction can be accomplished in situ by initially dispersing the silylated product formed in a polymeric binder, resulting in a film, and subsequently exposing this film to a hydrolysis solvent or its vapor. For causing the formation of the novel deuterated hydroxyl squaraine compositions of the present invention, hydrolysis is effected in substantially an identical manner with the exception that there is selected as the hydrolysis reactant, a deuterated material as illustrated hereinafter. Thus, when the hydrolysis of the silylated squaraine composition or silylated squaraine derivatives is effected in the presence of a solvent system containing deuterated water or deuterated alcohols there are obtained the novel deuterated hydroxyl squaraine derivatives as illustrated hereinbefore. These deuterated compositions can be incorporated as photoconductive pigments, for example, in photoresponsive devices similar to the devices illustrated herein with respect to the hydroxyl squaraine compositions.

The amount of silylation reactants selected is dependent upon a number of factors, including the specific reactants and solvents selected, the reaction temperature, the degree of purity of squaraine product desired and other reaction parameters involved. Generally, however, a slight excess of the theoretical amount of silylation reagent is used to achieve complete functionalization of the hydroxyl group or groups contained in the starting squaraine reactant. However, partial silylation of the hydroxyl squaraine reactants, followed by hydrolysis, can also be effected to obtain the hydroxyl squaraines of improved purity. Additionally, an effective but minimum amount of solvent is utilized to achieve the silylation reaction and to maximize yield of product. This amount, ranges for example, from about 5 milliliters to about 80 milliliters, and preferably from about 5 milliliters to about 35 milliliters for each gram of selected hydroxyl squaraine. Also, the hydrolysis of the silylated squaraine derivatives can be effected in a selected solvent system at an optimum temperature in order that the resulting reverted hydroxyl squaraine derivatives will have desirable particle sizes and improved morphological characteristics. The temperature selected for the silylation and hydrolysis can likewise vary depending on the other reaction parameters, generally however the silylations are accomplished at a temperature of from about zero degrees Centigrade to about 200 degrees Centigrade, while the hydrolysis reactions are accomplished at a temperature of from about −20 degrees Centigrade to about 120 degrees Centigrade.

The resulting products subsequent to the hydrolysis from the reaction mixture can be isolated and purified by various known techniques, including for example filtration, washing, evaporation, and crystallization. These products were characterized primarily by elemental analysis data, infrared analysis, NMR analysis, visible absorption spectroscopy and microscopy techniques, including scanning electron microscopy, transmission electron microscopy and photomicroscopy. Additionally, the chemical composition data generated from these techniques were substantially equivalent to the data available for the identical compounds prepared from the squaric acid process.

The hydroxyl squaraine derivatives, and deuterated hydroxyl squaraine derivatives prepared in accordance with the process of the present invention are of a small particle size ranging in diameter of from about less than 0.1 microns to about less than 1.0 microns. Small particle sizes enable the superior dispersion of these products in resinous binder compositions, thereby allowing excellent uniform photoconductive pigment coverage, high image resolution, good charge acceptance and superior photosensitivity for imaging devices containing these compositions, as compared to similar hydroxyl squaraines prepared by the known squaric acid process.

BRIEF DESCRIPTION OF THE DRAWINGS

For a better understanding of the present invention and further features thereof reference is made to the following detailed description of various preferred embodiments wherein.

DESCRIPTION OF THE PREFERRED EMBODIMENTS

Figures 1, 2:
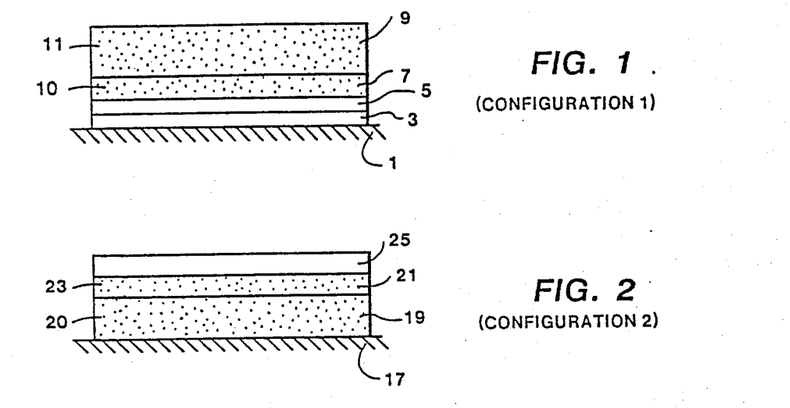
FIGS. 1 to 4 (configurations 1 to 4 respectively) are schematic cross-sectional views of photoresponsive devices of the present invention.

There is illustrated in FIG. 1 (configuration 1) a photoresponsive device comprised of a supporting substrate 1, an optional blocking layer 3, an optional adhesive layer 5, a photoconductive layer 7, comprised of the purified hydroxyl squaraine compositions prepared in accordance with the present invention, optionally dispersed in a resinous binder 10, and as a top layer 9, a charge transport or hole transport layer containing a transporting composition, such as an aromatic amine or an aromatic diamine, dispersed in a resinous binder composition, 11.

Illustrated in FIG. 2 (configuration 2) is a photoresponsive device comprised of a conductive substrate 17, such as aluminized Mylar, a hole transport layer 19, containing a material which will transport holes, including aromatic diamines and aromatic amines dispersed in a resinous binder 20, a photoconductive layer 21, comprised of the squaraine compositions prepared in accordance with the process of the present invention, optionally dispersed in a resinous binder, 23 and an optional protective overcoating layer 25.

Figure 3:
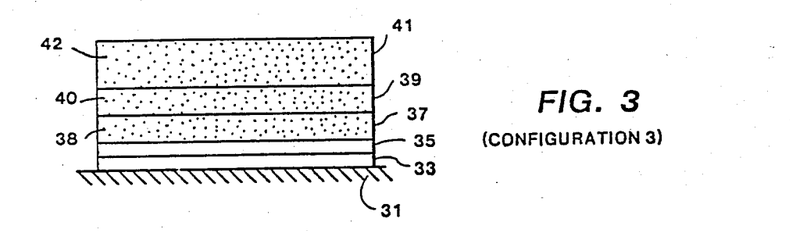

Illustrated in FIG. 3 (configuration 3) are photoresponsive devices useful in imaging and printing systems, comprised of a conductive substrate 31, an optional blocking layer 33, an optional adhesive layer 35, a photogenerating layer 37 comprised of inorganic or organic photogenerating pigments, optionally dispersed in a resinous binder 38, these pigments including metal phthalocyanines, metal free phthalocyanines, vanadyl phthalocyanines, selenium, selenium alloys, trigonal selenium and the like, layer 39 comprised of the squaraine compositions prepared in accordance with the process of the present invention, optionally dispersed in a resinous binder 40, and a charge transport layer 41, comprised of materials which will enable the transport of positive charges, including aromatic diamines and aromatic amines dispersed in resinous binder compositions, 42.

Figure 4:
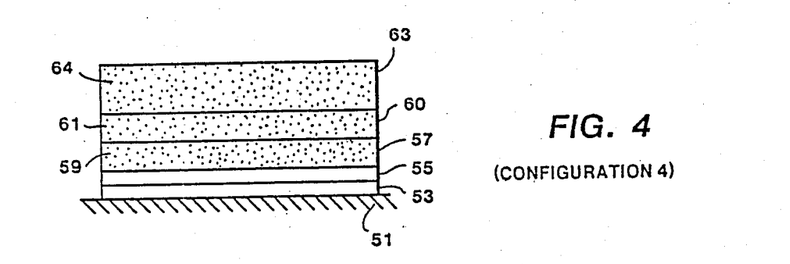

In FIG. 4, (configuration 4) there is illustrated a further photoresponsive device of the present invention comprised of a conductive supporting substrate of, for example, aluminized Mylar 51, an optional blocking layer 53, an optional adhesive layer 55, a photoconductive layer 57, comprised of the squaraine compositions prepared in accordance with the process of the present invention, optionally dispersed in a resinous binder 59 a photogenerating layer 60, comprised of organic photoconductive pigments or inorganic photoconductive pigments, optionally dispersed in a resinous binder 61, and as a top layer 63, a charge transporting substance, including an aromatic diamine or an aromatic amine dispersed in a resinous binder 64.

When incorporated into xerographic imaging and printing systems the devices of FIGS. 1, 3 and 4 are subjected to negative charging on the surface, while the device of FIG. 2 is positively charged.

Similar photoresponsive imaging members, and devices, as well as additional members are described for example in copending applications U.S. Ser. No. 487,935/83 entitled Overcoated Photoresponsive Devices, and U.S. Pat. No. 4,508,803 entitled Photoconductive Devices Containing Novel Squaraine Compositions, with the exception that in the copending applications the squaraines are not prepared in accordance with the process of the present invention. The disclosure of each of the copending applications is totally incorporated herein by reference. Moreover illustrative examples of materials that can be selected for each of the layers described in the Figures, as well as the thicknesses of these layers are disclosed in the referred to copending applications.

Preferred materials for the photogenerating pigments include metal phthalocyanines, metal-free phthalocyanines, and trigonal selenium, while preferred hole transport molecules are comprised of the diamine compositions as illustrated in the copending applications. More specifically examples of amine hole transport compositions are N,N'-diphenyl-N,N'-bis(alkylphenyl)-[1,1-biphenyl]-4,4'-diamine wherein alkyl is selected from the group consisting of methyl, such as 2-methyl, 3-methyl and 4-methyl, ethyl, propyl, butyl, hexyl and the like. With chloro substitution, the amine is N,N'-diphenyl-N,N'-bis(halophenyl)-[1,1'-biphenyl]-4,4'-diamine wherein the halo atom is 2-chloro, 3-chloro or 4-chloro. Resinous binders selected include materials such as those described in U.S. Pat. No. 3,121,006 the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials for the transport layer are polycarbonate resins having a molecular weight (Mw) of from about 20,000 to about 100,000 with a molecular weight in the range of from about 50,000 to about 100,000 being particularly preferred. Generally, the resinous binder contains from about 10 to about 75 percent by weight of the hole transport material, and preferably from about 35 percent to about 50 percent of this material. Preferred binder compositions for the photogenerating, or photoconductive layers include polyesters, polyvinylbutyral, Formvar ®, polycarbonate resins, especially those commercially available as Makrolon ®, polyvinyl carbazoles, epoxy resins, phenoxy resins, commercially available as poly(hydroxyether)resins, and the like.

Examples of overcoating layers for the imaging members illustrated are selenium alloys, silicone hardcoatings, and other related compositions. This layer can be of a thickness of from about 1 micron to about 2 microns.

The supporting substrates for the imaging members described may comprise a layer of insulating material such as an inorganic or organic polymeric material, a layer of an organic or inorganic material having a conductive surface layer thereon, or a conductive material such as, for example, aluminum, chromium, nickel, indium, tin oxide, brass or the like. Also there can be coated on the substrate as optional layers known hole blocking layers, like silane compositions, and an adhesive material, such as a polyester resin, commercially available for example from Goodyear Chemical Company. The substrate may be flexible or rigid and may have any of many different configurations, such as for example, a plate, a cylindrical drum, a scroll, an endless flexible belt and the like. Preferably, the substrate is in the form of an endless flexible belt.

The photoreceptor devices described can be prepared by a number of known methods, reference for example the copending applications indicated, the process parameters and the order of coating of the layers being dependent on the device desired. Thus, for example, a multilayered photoreceptor device can be prepared by vacuum sublimation or various solution coatings of the photoconducting layer on a supporting conductive substrate, with or without a blocking layer, and an interface adhesive layer, and subsequently depositing by solution coating the hole transport layer. In another process variant, the layered photoreceptor device can be prepared by providing the conductive substrate possessing a hole blocking layer and an optional adhesive layer, and applying thereto by solvent coating processes including solution spray coating, draw bar coating processes, laminating processes, or other methods, a photogenerating layer, a photoconductive composition comprised of the squaraines of the present invention, which squaraines are capable of enhancing the intrinsic properties of the imaging member in the infrared and/or visible range of the spectrum, and a hole transport layer.

The improved photoreceptor devices of the present invention can be incorporated into various imaging systems, including conventional xeographic imaging processes. Additionally, the improved photoreceptor devices of the present invention containing an inorganic photogenerating layer, and a photoconductive layer comprised of the hydroxyl squaraines of the present invention can function in imaging and printing systems with visible light and/or near infrared light. In this embodiment, the improved photoresponsive devices of the present invention may be either negatively charged or positively charged, depending on the configuration of the photoreceptor, exposed to light in a wavelength of from about 300 to about 950 nanometers, either sequentially simultaneously, or selectively, followed by developing the resulting image, and transferring to paper or other substrates. The above sequence may be repeated many times.

The invention will now be described in detail with reference to specific embodiments thereof, it being understood that these examples are intended to be illustrative only. The invention is not intended to be limited to the materials, conditions, or process parameters recited herein, it being noted that all parts and percentages are by weight unless otherwise indicated. Additionally with respect to the working Examples, as well as the specification and claims, reference to modified hydroxyl squaraines refer to compositions prepared by the process described in the present application, while the phrase unmodified hydroxyl squaraines refers to materials prepared by the known squaric acid condensation method described in the prior art.

EXAMPLE I

Bis(2-hydroxyl-4-N,N-dimethylaminophenyl)-squaraine (OH-Sq, 2.75 grams), N,N-dimethylformamide (DMF, 34.5 ml) and bis(trimethylsilyl)trifluoracetamide (BSTFA, 2.75 grams) were heated together with stirring at 60° C. under an argon atmosphere for 6.0 hours. The mixture was cooled to room temperature, and the resulting solid was collected by vacuum filtration under an argon atmosphere, followed by rinsing the product with a 10 volume percent solution of anhydrous diethyl ether in hexane. The product was then dried under vacuum at 40° C. for 1.5 hours resulting in 3.70 grams of bis(2-trimethylsiloxy-4-N,N-dimethylaminophenyl)squaraine (O-TMS-Sq), in the form of shiny, green-gold crystals.

Found: C, 62.92; H, 7.22, N, 5.89; O, 12.84; Si, 11.05. Calcd for: $C_{26}H_{36}N_2O_4Si_2$: C, 62.87; H, 7.30; N, 5.64; O, 12.88; Si, 11.31.

Infrared (Nujol): New peaks appeared at 914 and 853 $cm^{-1}$ and peaks at 1,400, 888 and 738 $cm^{-1}$ disappeared. $^1H$-NMR data was consistent with that of the expected silylated product.

EXAMPLE II

The process of Example I was repeated with the exception that there was selected as a replacement for the squaraine reactant (OH-Sq) bis(2-hydroxy-4-N,N-diethylaminophenyl)squaraine (OH-Et-Sq, 2.19 grams). Also 35.0 milliliters of DMF and 2.93 grams of BSFTA were used. The time of reaction was 3.5 hours. Bis(2-trimethylsiloxy-4-N,N-diethylaminophenyl)squaraine (O-TMS-EtSq) 3.84 grams was obtained as a green powder.

Found: C, 65.18; H, 8.02; N, 5.05; O, 11.41; Si, 9.96. Calcd for: $C_{30}H_{44}N_2O_4Si_2$: C, 65.18; H, 8.02; N, 5.07; O, 11.58; Si, 10.16.

Infrared (Nujol): New peaks appeared at 1,586, 1,150, 976, 851 and 767 $cm^{-1}$ and peaks at 1,536, 1120 and 956 $cm^{-1}$ disappeared. $^1H$-NMR data was consistent with that of the expected silylated product.

EXAMPLE III

The process of Example I was repeated with the exception that there was selected as a replacement for the squaraine reactant (OH-Sq), bis(2-hydroxy-6-methyl-4-N,N-dimethylaminophenyl)squaraine (OH-ME-Sq, 0.600 grams). Also 8.0 milliliters of DMF, and 0.533 grams of BSFTA were used. The time of reaction was 5.0 hours. Bis(2-trimethylsiloxy-6-methyl-4-N,N-dimethylaminophenyl)squaraine (O-TMS-MeSq) 0.650 grams was isolated as a green-grey powder.

Infrared (Nujol): New peaks appeared at 1,593, 1,264 and 1108 $cm^{-1}$ and peaks at 1,611, 1,235, 1,202, 1095 and 871 $cm^{-1}$ disappeared. $^1H$-NMR data was consistent with that of the expected silylated product.

EXAMPLE IV

The squaraine composition prepared in Example I (O-TMS-Sq), 1.50 grams, was stirred with tetrahydrofuran (25 ml) for 5.0 minutes, Methanol, (25.0 ml) and water (1.0 ml) were added to the mixture which was then stirred at 60° C. for 2.0 hours. The resulting solid was collected from the warm mixture by vacuum filtration and rinsed with methanol. The product was dried under vacuum at 60° C. for 2.0 hours yielding 1.11 grams of the modified hydroxyl squaraine, bis(2-hydroxy-4-N,N-dimethylaminophenyl)squaraine(OH-Sq), as a blue grey powder.

Found: C, 68.28; H, 5.69; N, 8.02; O, 17.81. Calcd. for $C_{20}H_{20}N_2O_4$: C, 68.17; H, 5.72; N, 7.95; O, 18.16

Infrared (Nujol) data was identical to that for the unmodified OH-Sq.

Transmission Electron Microscopy (TEM) and photomicroscopy results indicate that the modified OH-Sq pigment, prepared in accordance with Example IV contains a high population of fine, acicular particles/-crystallites of approximately 100 Angstroms width and 1,000 Angstroms length and some denser acicular particles/crystallites ranging in length of from 0.2 um to 1.8 um. In contrast, unmodified OH-Sq (obtained from the squaric acid synthesis) has a particle/crystallite size range of from approximately 1.2 um to 27.5 um in length, as determined by TEM and photomicroscopy.

EXAMPLE V

The squaraine composition prepared in Example II, (O-TMS-EtSq, 1.43 grams), was stirred with methanol (50 ml) and water (0.1 ml) at 60° C. for 3.5 hours. The resulting solid product was collected from the mixture by vacuum filtration, and rinsed with methanol. The product was then dried under vacuum at 45° C. for 1.5 hours yielding 1.05 grams of the modified bis(2-hydroxy-4-N,N-diethylaminophenyl)squaraine, (OH-EtSq), as a green-gold powder.

Found: C, 70.35; H, 7.06; N, 6.73; O, 15.34. Calcd for $C_{24}H_{28}N_2O_4$: C, 70.57; H, 6.91; N, 6.86; O, 15.67.

Infrared (Nujol) and $^1$H-NMR data were identical to that of unmodified OH-Et-Sq.

TEM and photomicroscopy measurements indicated that the particle/crystallite size of the squaraine composition prepared in accordance with Example V was less than 10 percent of the original particle/crystallite size of the untreated, or unmodified bis(2-hydroxy-4-N,N-diethylaminophenyl)squaraine. This reduction in particle size enables more uniform dispersion, or coverage of the hydroxy squaraine in the photoconductive layer, when these compositions are incorporated into imaging members.

EXAMPLE VI

The process of Example V was repeated with the exception that there was selected as the squaraine reactant, O-TMS-Me(methyl)Sq, bis(2-hydroxy-6-methyl-4-N,N-diethylaminophenyl)squaraine, prepared in accordance with Example III (0.1749 grams), with the hydrolysis solvents being methanol (10.0 ml) and water (0.5 ml). The resulting mixture was stirred at 22° C. for 3 hours. After rinsing the isolated product with a 20 percent solution of water in methanol, there was recovered as a light green powder the modified squaraine OH-Me-Sq (0.131 grams). Infrared (Nujol) data was identical to that of unmodified OH-Me-Sq. The modified OH-Me-Sq has needle-like particles/crystallites 0.5–1.0 um in length, and 0.1 um wide as compared with the unmodified OH-Me-Sq which has a particle/crystallite size of 100 um in length and 20 um wide, as determined by TEM, and photomicroscopy.

In the following examples there is detailed the preparation of photoresponsive imaging members by coating dispersions of photoconductive pigments in polymeric binders, and the coating of polymeric solutions of the charge transport molecule indicated, on aluminized Mylar, which is about 3 mils in thickness. Moreover in all of the examples the aluminized Mylar was overcoated in a thickness of 0.05 um., with an adhesive material of the polyester duPont 49,000. Mylar is a tradename for a poly(ethylene terephthalate) film available from duPont. In each example the charge transport molecule selected was N,N'-diphenyl-N,N'-bis(3-methylphenyl)-1,1'-biphenyl-4,4'-diamine, 40 weight percent, dispersed in 60 percent by weight of the polycarbonate Makrolon, dissolved in dichloromethane. For the coating of the solutions there was selected a known Bird applicator.

EXAMPLE VII

A dispersion of photoconductive pigment was prepared by adding 0.100 grams of the unmodified squaraine composition OH-Sq, and 50 grams of ⅛ inch No. 302 stainless steel shot to a solution of 0.400 grams of Goodyear Vitel PE-200 polyester resin and 8.0 ml of dichloromethane in a 2 oz. bottle followed by shaking the resulting mixture on a paint shaker. The pigment dispersion product was then coated onto an aluminized Mylar substrate with a 1.0 mil gap Bird-type applicator bar. The coating was air-dried and followed by drying under vacuum at 100° C. for 2.5 hours.

There was then coated on the above prepared photoconductive layer with a Bird applicator a charge transport layer containing 40 percent by weight of N,N'-diphenyl-N,N'-bis(3-methylphenyl)-1,1'-biphenyl-4,4'-diamine, dispersed in 60 percent by weight of the polycarbonate resinous binder Makrolon.

EXAMPLE VIII

A photoresponsive device was prepared by repeating the procedure of Example VII with the exception that there was selected as the photoconductive pigment the modified hydroxyl squaraine as prepared in Example IV in place of the unmodified hydroxyl squaraine.

EXAMPLE IX

A photoresponsive device was prepared by repeating the procedure of Example VII with the exception that there was first coated with a Bird applicator on the aluminized Mylar substrate a photogenerating layer containing trigonal selenium dispersed in a poly(N-vinylcarbazole) solution. This photogenerating layer was prepared by dispersing 7.5 volume percent of finely milled trigonal selenium in a poly(N-vinylcarbazole) solution containing a mixture of tetrahydrofuran:toluene (1:1). The thickness of this layer was about two microns.

EXAMPLE X

A photoresponsive device was prepared by repeating the procedure of Example IX with the exception that there was selected as the photoconductive pigment, 0.1 grams, of the modified hydroxyl squaraine as prepared in accordance with Example IV.

EXAMPLE XI

A photoresponsive device was prepared by repeating the procedure of Example VII with the exception that there 0.126 grams of unmodified hydroxyl squaraine was selected, and there was used as the pigment binder resin, PE-100 polyester (0.380 grams), available from Goodyear Chemical.

EXAMPLE XII

A photoresponsive device was prepared by repeating the procedure of Example VII with the exception that 0.126 grams of a modified hydroxyl squaraine as prepared in accordance with Example IV was selected, and in place of PE-200 there was selected the polyester PE-100 (0.380 grams).

EXAMPLE XIII

A photoresponsive device was prepared by repeating the procedure of Example VII with the exception that there was first coated on the aluminized Mylar substrate, a hole transport layer containing the specific diamine indicated, followed by coating thereover a polymeric dispersion of a photoconductive hydroxyl squaraine pigment.

EXAMPLE XIV

A photoresponsive device was prepared by repeating the procedure of Example XIII with the exception that there was selected 0.12 grams of the modified hydroxyl squaraine as prepared in accordance with the procedure of Example IV, as a replacement for the unmodified hydroxyl squaraine.

EXAMPLE XV

A photoresponsive device was prepared by repeating the procedure of Example XIII with the exception that 0.166 grams of the unmodified hydroxyl squaraine was selected, and 0.3808 grams of the polycarbonate Makrolon was used as a replacement for the PE-200 composition.

EXAMPLE XVI

A photoresponsive device was prepared by repeating the procedure of Example XIII with the exception that 0.177 grams of the modified hydroxyl squaraine as prepared in accordance with Example IV was selected, and 0.3808 grams of the resinous polycarbonate binder Makrolon was used as a replacement for the PE-200 composition.

Several of the above prepared photoresponsive devices were then electrically tested by charging them with a constant voltage corotron and photodischarging the devices with a specific wavelength (for example 597 nm or 800 nm light.) The charging and photodischarging processes were monitored by an electrometer and recorded on a strip chart recorder. The surface potential of the photoresponsive device just prior to the light exposure is represented by $V_{DDP}$. The maximum sensitivity was calculated as the maximum photodischarge rate divided by the radiant power of the light, and the energy to $\frac{1}{2}V_{DDP}$ was the light energy required to discharge the device to $\frac{1}{2}$ of its original surface potential value.

| ELECTRICAL DATA OF PHOTORECEPTORS CONTAINING MODIFIED AND UNMODIFIED HYDROXYL SQUARAINE (OH—Sq) | | | | | |
|---|---|---|---|---|---|
| | SURFACE POTENTIAL V | | MAXIMUM SENSITIVITY V-Cm$^2$/Erg | | ENERGY to $\frac{1}{2}$ V$_{DDP1}$ Erg/cm$^2$ |
| EXAMPLE | V$_{DDP}$ | at 597 nm | at 800 nm | at 597 nm | at 800 nm |
| VII a, c, f, i | −895 | 37.1 | 42.2 | 14.9 | 13.11 |
| VIII b, c, f, i | −895 | 63.4 | 86.8 | 8.35 | 6.18 |
| IX a, d, f, i | −900 | 52.9 | 58.6 | 10.0 | 10.6 |
| X b, d, f, i | −895 | 74.8 | 94.4 | 7.43 | 6.36 |
| XI a, c, g, j | −900 | 41.9 | 51.4 | 12.8 | 10.8 |
| XII b, c, g, j | −895 | 87.4 | 116.6 | 6.19 | 4.79 |
| XIII a, e, f, i | 900 | 40.4 | 37.0 | 13.6 | 15.0 |
| XIV b, e, f, i | 895 | 43.6 | 49.1 | 13.6 | 13.3 |
| XV a, e, h, k | 710 | 56.8 | 62.8 | 6.67 | 7.71 |
| XVI b, e, h, k | 510 | 74.8 | 81.5 | 4.59 | 3.90 | a is unmodified OH-Sq; b is modified (by the invention process) OH-Sq, c is configuration 1, d is configuration 3, e is configuration 2, f is weight loading of squaraine=20 percent, g is weight loading of squaraine=25 percent, h is weight loading of squaraine=30 percent, i is PE-200 binder, j is PE-100 binder, k is Makrolon binder, l is energy required to discharge one-half of the initial surface potential.

The larger the maximum sensitivity number the more desirable discharge is achieved, that is, the discharge rate is greater with the same amount of light. A smaller value of energy to $\frac{1}{2}V_{DDP}$ represents a more efficient photodischarge.

EXAMPLE XVII

Bis(2-trimethylsilyloxy-4-N,N-dimethylaminophenyl)squaraine (O-TMS-Sq, 0.250 gram) obtained by the process of Example I, was stirred under argon gas with deuterated methanol- d$_1$, (99.5 percent isotopic purity, 11.0 ml) and deuterium oxide (99.96 percent isotopic purity, 0.50 ml), at 25° C. for 2.5 hours. The solid was collected by vacuum filtration under vacuum and rinsed with diethyl ether. The collected material was dried under vacuum at 45° C. for 2 hours yielding 0.194 gram of bis(2-deuteriohydroxy-4-N,N-dimethylaminophenyl)squaraine (deuterated hydroxyl squaraine, OD-Sq) as a green solid.

Calcd for $C_{20}H_{18}D_2N_2O_4$: 67.78; H and D, 6.26. Found: C, 67.86; H and D, 6.65.

EXAMPLE XVIII

A photoresponsive device was prepared by repeating the procedure of Example VII with the exception that the bis-(2-deuteriohyroxy-4-dimethylaminophenyl)-squaraine, obtained by the process of Example XVII, (OD-Sq), 0.100 grams, was selected in place of the unmodified hydroxyl squaraine.

EXAMPLE XIX

A photoresponsive device was prepared by repeating the procedure of Example IX with the exception that there was selected as the photoconductive pigment 0.100 grams of the deuterated hydroxyl squaraine OD-Sq, obtained by the process of Example XVII, in place of the unmodified hydroxyl squaraine.

EXAMPLE XX

A photoresponsive device was prepared by repeating the procedure of Example XIII with the exception that 0.100 grams of the deuterated hydroxyl squaraine, OD-Sq, obtained by the process of Example XVII, was selected in place of the unmodified hydroxyl squaraine.

Electrical tests were conducted for the devices Examples XVIII and XIX with the following results:

| ELECTRICAL DATA OF PHOTORECEPTORS DEUTERATED HYDROXYL -d$_2$—SQUARAINE (compound obtained from Example XVII) | | | | | |
|---|---|---|---|---|---|
| | SUYRFACE POTENTIAL V | | MAXIMUM SENSITIVITY V-Cm$^2$/Erg | | ENERGY to $\frac{1}{2}$ V$_{DDP}$ Erg/Cm$^2$ |
| EXAMPLE | V$_{DDP}$ | at 597 nm | at 800 nm | at 597 nm | at 800 nm |
| XIII[a] | −890 | 56.4 | 73.3 | 9.52 | 7.47 |
| XIX[b] | −885 | 64.7 | 84.1 | 9.19 | 7.19 |
| XX[c] | 907 | 30.1 | 34.1 | 21.8 | 23.4 |

[a] configuration 1,
[b] configuration 3,
[c] configuration 2.

Although the invention has been described with reference to specific embodiments, it is not intended to be limited thereto, rather those skilled in the art will recognize that variations and modifications may be made therein which are within the spirit of the present invention and within the scope of the following claims.

We claim:

1. A photoresponsive device comprised of a conductive supporting substrate, a photoconductive layer comprised of the hydroxyl squaraines, and a top hole transporting layer comprised of a transporting molecule dispersed in a resinous binder, wherein the squaraines are prepared by affecting functionalization of a hydroxyl squaraine in an organic solvent system wherein the hydroxyl groups are silylated, and thereafter subjecting the resulting silylated products to hydrolysis enabling conversion to purified squaraine compositions.

2. A photoresponsive device comprised of a conductive supporting substrate, a hole transporting layer comprised of a transporting molecule dispersed in a resinous binder, and a top photoconductive layer comprised of the hydroxyl squaraines prepared by affecting functionalization of a hydroxyl squaraine in an organic solvent system wherein the hydroxyl groups are silylated, and thereafter subjecting the resulting silylated products to hydrolysis enabling conversion to purified squaraine compositions.

3. A photoresponsive device in accordance with claim 2 wherein there is further included in contact with the photoconductive layer a polymeric protective overcoating layer.

4. A photoresponsive device in accordance with claim 1 wherein the squaraine is a modified bis(2-hydroxy-N,N-dimethylaminophenyl)squaraine.

5. A photoresponsive device in accordance with claim 2 wherein the squaraine is a modified bis(2-hydroxy-N,N-dimethylaminophenyl)squaraine.

6. A photoresponsive device in accordance with claim 1 wherein the charge transporting molecule is N,N'-diphenyl-N,N'-bis-3-methylphenyl-1,1'-biphenyl-4,4'-diamine.

7. A photoresponsive device in accordance with claim 2 wherein the charge transporting molecule is N,N'-diphenyl-N,N'-bis-3-methylphenyl-1,1'-biphenyl-4,4'-diamine.

8. A photoreceptor device comprised of a conductive supporting substrate, a photogenerating layer comprised of organic photogenerating pigments or inorganic photogenerating pigments, dispersed in a resinous binder, a photoconductive layer comprised of the hydroxyl squaraines, and as a top layer a charge transporting layer comprised of charge transporting molecules optionally dispersed in a resinous binder, wherein the squaraines are prepared by affecting functionalization of a hydroxyl squaraine in an organic solvent system wherein the hydroxyl groups are silylated, and thereafter subjecting the resulting silylated products to hydrolysis enabling conversion to purified squaraine compositions.

9. A photoresponsive device in accordance with claim 8 wherein the photoconductive layer is situated between the optional adhesive layer and the organic photogenerating layer.

10. A photoresponsive device in accordance with claim 8 wherein the hydroxyl squaraine is a modified bis(2-hydroxy-4-N,N-dimethylaminophenyl)squaraine.

11. A photoresponsive device in accordance with claim 9 wherein the hydroxyl squaraine is a modified bis(2-hydroxy-4-N,N-dimethylaminophenyl)squaraine.

12. A photoresponsive device in accordance with claim 8 wherein the hole transporting molecule is N,N'-diphenyl-N,N'-bis(3-methylphenyl) 1,1'-biphenyl-4,4'-diamine.

13. A photoresponsive device in accordance with claim 10 wherein the hole transporting molecule is N,N'-diphenyl-N,N'-bis(3-methylphenyl) 1,1'-biphenyl-4,4'-diamine.

14. A photoresponsive device in accordance with claim 8 wherein the photogenerating pigment is selected from the group consisting of selenium, selenium alloys, trigonal selenium, metal phthalocyanines, metal free phthalocyanines, and vanadyl phthalocyanine.

15. A photoresponsive device in accordance with claim 10 wherein the photogenerating pigment is selected from the group consisting of selenium, selenium alloys, trigonal selenium, metal phthalocyanines, metal free phthalocyanines, and vanadyl phthalocyanine.

16. A photoresponsive device in accordance with claim 1 wherein there is further included therein a blocking layer.

17. A photoresponsive device in accordance with claim 1 wherein there is further included therein an adhesive layer.

18. A photoresponsive device in accordance with claim 2 wherein there is further included therein a blocking layer.

19. A photoresponsive device in accordance with claim 2 wherein there is further included therein an adhesive layer.

20. A photoresponsive device in accordance with claim 8 which includes therein a silane interfactial layer.

21. A photoresponsive device in accordance with claim 8 including therein an adhesive layer.

22. A photoresponsive device in accordance with claim 1 wherein the squaraines are acicular, and about 100 Angstroms in width, and about 1,000 Angstroms in length.

23. A photoresponsive device in accordance with claim 1 wherein the squaraines are acicular, and about 0.2 microns in width, and about 18 microns in length.

* * * * *